United States Patent
Kraus et al.

[11] Patent Number: 6,053,032
[45] Date of Patent: Apr. 25, 2000

[54] SYSTEM AND METHOD FOR DETERMINING A DEPOSITION RATE IN A PROCESS STREAM INDICATIVE OF A MASS BUILD-UP AND FOR CONTROLLING FEED OF A PRODUCT IN THE PROCESS STREAM TO COMBAT SAME

[75] Inventors: Paul R. Kraus, Bolingbrook; Jeffrey P. Chamberlain, Wheaton; Linda R. Robertson, St. Charles; Barbara E. Moriarty, Woodridge, all of Ill.

[73] Assignee: Nalco Chemical Company, Naperville, Ill.

[21] Appl. No.: 09/009,968

[22] Filed: Jan. 21, 1998

Related U.S. Application Data

[62] Division of application No. 08/787,881, Jan. 23, 1997, abandoned, which is a continuation of application No. 08/421,206, Apr. 13, 1995, abandoned.

[51] Int. Cl.[7] .................................................. G01N 33/00
[52] U.S. Cl. .......................... 73/61.62; 73/61.49; 137/2
[58] Field of Search ........................ 73/86, 61.62, 61.49, 73/64.53; 137/2, 3, 87.1, 88, 93

[56] References Cited

U.S. PATENT DOCUMENTS

| | | | |
|---|---|---|---|
| 3,715,911 | 2/1973 | Chuan | 73/24.03 |
| 3,863,495 | 2/1975 | Schulz et al. | 73/61.58 |
| 4,547,648 | 10/1985 | Longeway | 219/121.41 |
| 4,788,466 | 11/1988 | Paul et al. | 73/54.41 |
| 5,112,642 | 5/1992 | Wajid | 427/70 |
| 5,135,852 | 8/1992 | Ebersole et al. | 435/39 |
| 5,201,215 | 4/1993 | Granstaff et al. | |
| 5,208,162 | 5/1993 | Osborne et al. | 436/6 |
| 5,369,033 | 11/1994 | DiMilia et al. | 436/148 |
| 5,484,626 | 1/1996 | Storjohann et al. | 427/8 |
| 5,487,981 | 1/1996 | Nivens et al. | 435/30 |

OTHER PUBLICATIONS

Beck, Ralf et al. "Influence of the Surface Microbalance on the Coupling Between a Quartz Oscillator and a Liquid," in *J. Electrochem. Soc.*, vol. 139, Feb. 1992, pp. 453–461.

Benje, Michael et al. "An Improved Quartz Microbalance: Applications to the Electrocrystallization and—dissolution of Nickel" in *Ber. Bunsenges Phys. Chem.*, 90, VCH Verlagsgesellschaft mbH, 1986, pp. 435–439.

"Electrochemical Quartz Nanobalance," brochure by Elchema on the Model EQCN–500, Potsdam, NY.

"The Smart Plating and Etching Coupon System" brochure by Maxtek, Inc., Torrance, CA.

*Primary Examiner*—Richard A. Moller
*Attorney, Agent, or Firm*—Hill & Simpson

[57] ABSTRACT

A system and a method are provided for detecting and monitoring changes in frequency in a process stream. At least one probe is placed in the process stream that is capable of detecting a change in frequency due to a build-up of mass on the probe from scale, corrosion, biofilm or the like in the process stream. A processor receives the signal produced by the probe to produce an output signal indicative of the change in frequency which is proportional to mass detected by the probe. A feeder is capable of feeding a product into the process stream as a result of the detected change in frequency of the probe to combat the mass build-up from scale, corrosion, biofilm or the like in the process stream. The system and method are further capable of measuring anti-scalant, corrosion inhibitor, biocide efficacy and controlling product feed into the process stream based on the determined efficacy.

8 Claims, 3 Drawing Sheets

SYSTEM AND METHOD FOR DETERMINING A DEPOSITION RATE IN A PROCESS STREAM INDICATIVE OF A MASS BUILD-UP AND FOR CONTROLLING FEED OF A PRODUCT IN THE PROCESS STREAM TO COMBAT SAME

This application is a division of Ser. No. 08/787,881 filed Jan. 23, 1997 abandoned, which is a continuation of Ser. No. 08/421,206 filed Apr. 13, 1995 abandoned.

BACKGROUND OF THE INVENTION

The present invention generally relates to a system for monitoring formation of deposits in systems. More specifically, the present invention relates to a quartz crystal microbalance (QCM) monitor to monitor deposition rate and amount in flowing industrial waters and the like, and can further be adapted for use as a system and a method for determining the effect of biocides or other non-toxic treatments on biofilm formation as well as the effect of antiscalants on scale deposition. Still further, the invention relates to real time measurement of the efficacy of scale control compounds in process water streams and controlling chemical feed pump rates as a function of the scale control compounds, particularly in process water streams.

It is, of course, generally known to monitor the effect of chemical treatments, such as biocides or antiscalants, against the planktonic population of industrial waters, such as, for example, by population kill studies. However, no systems are known for monitoring the effect of treatment chemicals against sessile microorganisms. It is, however, the sessile population that causes the fouling problems.

Standard methods only indirectly give information about the fouling populations giving rise to the fouling problems. Traditional methods for measuring the rate and quantity of scale deposition require the use of coupons directly immersed into the process stream. This prevents the rates to be measured in real time and delays the response time in which to effect the process stream when fouling occurs.

A need, therefore, exists for an improved system and method for measuring the rate of scale deposition in a flowing stream wherein the monitoring occurs in real time. Moreover, a need exists for an improved system and method that measures in real time the efficacy of scale control compounds in process water streams and controls chemical feed pump rates as a function of the scale, control efficacy, particularly for process water streams.

SUMMARY OF THE INVENTION

The present invention provides a system and a method for monitoring mass build-up from scale, biofilm, corrosion, or the like, in a process stream. The present invention further relates to a system and a method for feeding a product into the process stream as a result of a detected change in frequency on a probe placed in the process stream indicative of a build-up of a mass on the probe and, hence, in the process stream.

In an embodiment of the present invention, a system is provided for monitoring mass build-up from scale, fouling from corrosion products, or the like, in a process stream. The system has a probe placed in the process stream capable of detecting a change in frequency due to the build-up on the probe and producing a signal indicative thereof. A processing means receives the signal produced by the probe to produce an output signal indicative of the change in frequency wherein the output signal is proportional to mass detected by the probe.

In an embodiment, the system has a display means operatively connected to the processing means capable of displaying the mass detected on the probe.

In an embodiment, an input means is operatively connected to the processing means.

In an embodiment, a real time clock is operatively connected to the processing means.

In an embodiment, the system has at least one additional probe placed in the process stream capable of detecting a change in frequency at another point in the process stream due to build-up on the at least one additional probe and producing a signal indicative thereof.

In an embodiment, feeding means is operatively connected to the processing means and is capable of feeding a product into the process stream as a result of the detected change in frequency of the probe.

In an embodiment, the mass is calculated by multiplying a probe factor by a change in frequency detected by the probe.

In another embodiment of the present invention, a method is provided for monitoring a change in frequency of a probe in a process stream, the change in frequency due to mass build-up of scale, fouling from corrosion, or the like, on the probe in the process stream. The method comprises the steps of: providing the probe in the process stream; and detecting changes in the frequency of the probe wherein the frequency is indicative of the mass build-up on the probe.

In an embodiment, the method further comprises the step of feeding a product into the process stream as a result of the detected change. The feeding occurs after a predetermined magnitude of change in the frequency indicative of a mass build-up on the probe.

In an embodiment, the method further comprises the step of displaying the detected change in the mass on the probe.

In an embodiment, the method further comprises the step of providing at least one additional probe in the process stream wherein each of the at least one additional probes is capable of detecting a change in frequency.

In an embodiment, the method further comprises the step of providing a real time clock. The real time may be marked based on an associated change in frequency from a signal produced by the real time clock.

In an embodiment, the method further comprises the step of calculating the mass of the build-up using the detected change in the frequency of the probe.

In another embodiment of the present invention, a system is provided for feeding a product into a process stream. The system has a sensing means in communication with the process stream capable of detecting a change in the frequency in the process stream and producing a signal indicative of the change. A processing means receives the signal from the sensing means and is capable of producing a signal indicative of a quantity of mass on the sensing means in the process stream. Feeding means is operatively connected to the processing means and is capable of receiving the signal from the processing means indicative of the quantity of mass wherein the feeding means feeds the product into the process stream upon receipt of the signal.

In an embodiment, the feeding means feeds the product into the process means only due to a predetermined magnitude of the signal indicative of a predetermined quantity of mass.

In an embodiment, a display means is operatively connected to the processing means capable of displaying the change in frequency, the quantity of mass and/or scaling rate (e.g. $\mu g/hr$).

In another embodiment of the present invention, a system is provided for measuring anti-scalant efficacy on-line in a process stream. The system has a first sensing means detecting frequency change in the process stream and producing a signal indicative thereof. A processing means receives the signal from the first sensing means and produces a feed signal. Feeding means is responsive to the feed signal and is capable of feeding a product into the process stream as a result of the feed signal. A second sensing means is capable of detecting frequency change in the process stream after feeding the product into the processing means and producing a signal indicative thereof wherein the processing means is capable of receiving the signal from the second sensing means to compare with the signal from the first sensing means to provide an indication of the efficacy of the product in the process stream.

In an embodiment, an output means is capable of displaying the frequency changes and the efficacy.

In another embodiment of the present invention, a method is provided for controlling product feed into a process stream. The method comprises the steps of: monitoring scale deposition on a first probe placed in the process stream and producing a first signal indicative thereof; feeding a product into the process stream; monitoring scale deposition on a second probe placed in the process stream after the product is fed in the process stream and producing a second signal indicative thereof; determining efficacy of the product in the process stream by comparing the first signal with the second signal; and controlling feed of product based on the determined efficacy.

In an embodiment, the method determines efficacy in real time.

In an embodiment, the method further comprises the step of adjusting the feed to attain an acceptable scale growth inhibition level.

It is, therefore, an advantage of the present invention to provide a system and a method that is capable of measuring the rate of scale deposition in a flowing stream.

Another advantage of the present invention is to provide a system and a method for measuring the rate of scale deposition in a flowing stream monitored in real time.

A still further advantage of the present invention is to provide a system and a method for measuring the rate of scale formation that is simple to implement.

Yet another advantage of the present invention is to provide a system and a method for monitoring the rate of scale deposition in situ in a flowing stream.

Moreover, an advantage of the present invention is to provide a system and a method that monitors the effect of scale control chemicals directly within the process stream and adjustments may be made to the process as a result of the output.

A still further advantage of the present invention is to provide a system and a method for determining the effect of biocides or other non-toxic treatments on biofilm formation.

And, another advantage of the present invention is to provide a system and a method that is capable of screening several products at the same time.

A still further advantage of the present invention is to provide a system and a method that demonstrates the effect of both toxic biocides and non-toxic dispersants in preventing microbial adhesions.

Yet another advantage of the present invention is to provide a system and a method that is economical, rapid and easy to use.

A still further advantage of the present invention is to provide a system and a method that provides wide applicability to any waters subject to biological fouling.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to an on-line field-based quartz crystal microbalance (QCM) to monitor scale or biofilm deposition.

The QCM monitor of the present invention decreases the time required for measuring deposit growth, such as inorganic scales and biofilms, on a surface.

To this end, the QCM monitor accepts inputs from a plurality of separate probes that includes a non-volatile memory and has an analog output signal proportional to an interfacial mass detected at each probe. The QCM monitor also includes date and time stamps, the data of which is acquired using an on-board real time clock. Input may be accepted by the QCM monitor through a local keypad or through a remote computer interface.

Figure 1:
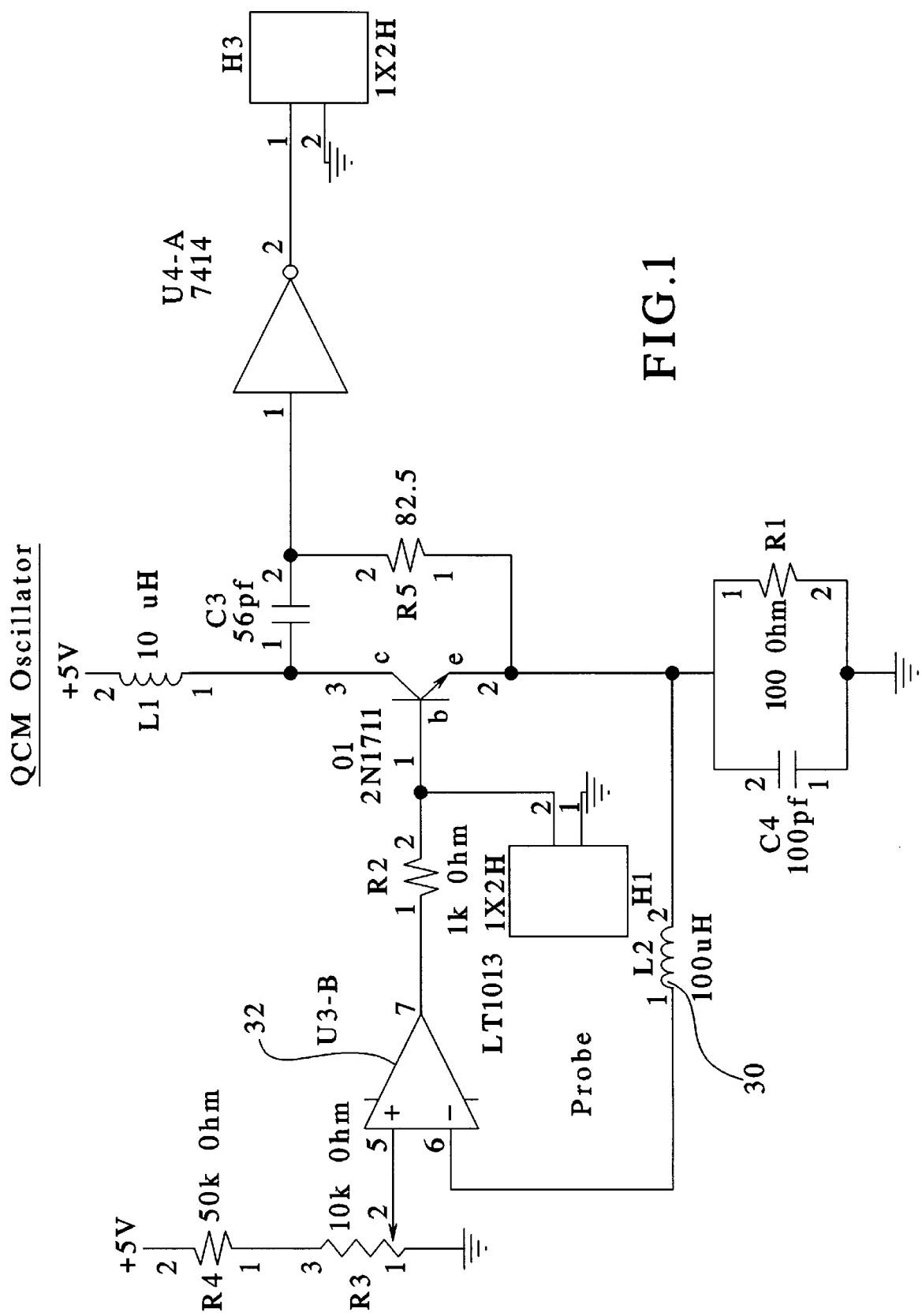
FIG. 1 illustrates an embodiment of a circuit diagram of an oscillator/probe of the present invention.

Referring now to the drawings, FIG. 1 illustrates an oscillator circuit that is used to drive a QCM probe. The oscillator circuit maintains a constant potential across a piezoelectric crystal to provide stable oscillations. A TTL output is attained using a Schmitt trigger as illustrated.

Figure 2:
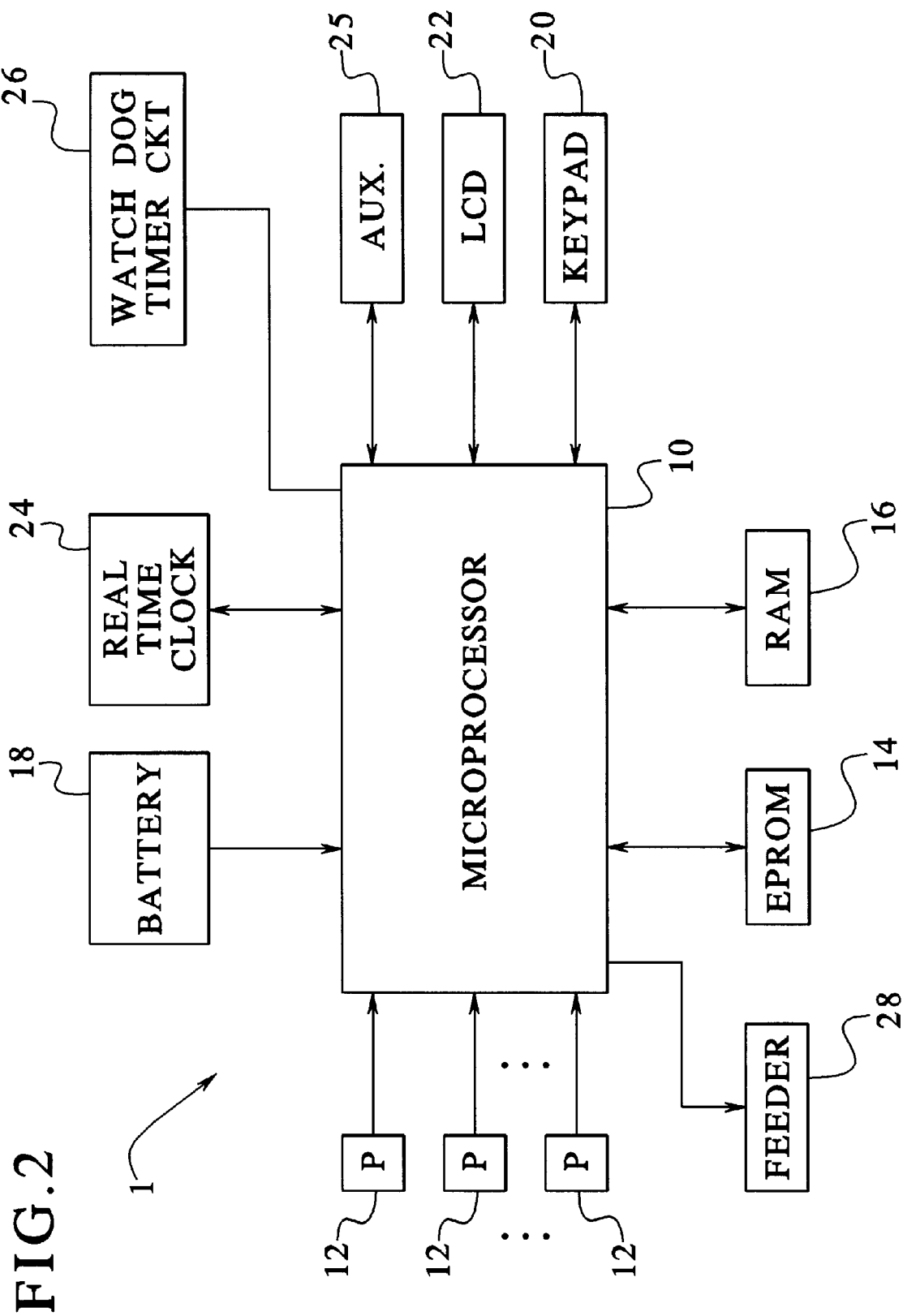
FIG. 2 illustrates a black box diagram of an embodiment of the system of the present invention.

A QCM monitor 1 is generally illustrated in FIG. 2. As shown, a microprocessor 10 is implemented to receive inputs from one or more probes 12. The microprocessor 10 includes both an EPROM 14 and a RAM 16. The microprocessor 10 further includes a battery 18, preferably an on-board lithium battery, which may be implemented as a battery backup for the RAM 16. This ensures that data stored in the RAM 16 will not be lost in the event of power failure.

The microprocessor 10 includes at least one port for interface with a keypad 26 and another port for interface with an LCD 22 or other display. Another auxiliary port is provided for necessary hook up of an auxiliary device 25, such as a personal computer. The microprocessor 10 also has a real time clock 24 to date/time stamp data and store the same in the RAM 16. A watch dog timer circuit 26 is also provided to reset the microprocessor 10 if the watch dog is not reset within a preset time.

In an embodiment, a reset period of 1.6 seconds is implemented with the monitor. The QCM monitor 1 is controlled by software programmed into the EPROM 14. A feeder 28 is further provided to control feeling of one or more compounds into the process stream to be described hereinafter.

Referring again to FIG. 1, a schematic diagram of the oscillator/probe 12 is illustrated having an inductor 30 provided at an inverting input of an emitter follower circuit 32. As a result, the effect of high frequency oscillations on a potential applied to a probe crystal is minimized. The inductor 30 is capable of maintaining a constant current input at the operational amplifier 32 by filtering out any high frequency oscillations. As a result, a constant potential across the piezoelectric crystal may be achieved.

A Schmitt trigger 34 is further provided to convert an analog output signal of the oscillator to a digital TTL signal. The digital signal transmitted through the cable to the frequency counting circuit has a greater immunity to electrical and magnetic noise corruption emanating from the environment as compared to an analog signal.

As a result of the design of the oscillator circuitry, the stability of the probe is increased. A constant potential may be applied to the crystal to provide enhanced oscillation stability as the interfacial mass on the crystal is increased. The TTL output signal of the oscillator circuit increases the quality of signal transmission from the oscillator/probe to the QCM monitor.

Figure 3:
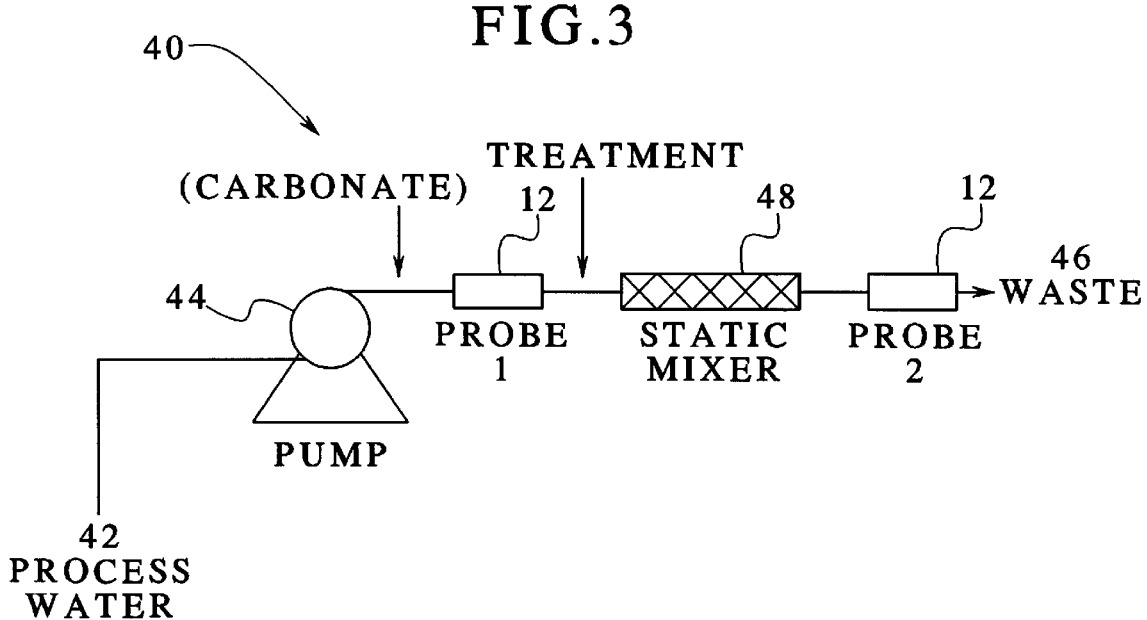
FIG. 3 illustrates a diagram of an embodiment of a flow system used to measure scale deposition.

Referring now to FIG. 3, a flow system 40 is illustrated. The flow system 40 measures scale deposition and inhibition using multiple QCM probes 12. The flow system 40 may be used in, for example, mining and mineral processing applications, and may be fashioned as a flow manifold. Process water 42 may be pumped in the system 40 by a pump 44. The probes 12 are located along the process stream between the input of the process water 42 and its output waste 46. A static mixer 48 may also be provided in the system 40 to mix the process stream following subjecting the stream to additives and/or other treatment. The probes 12 measure the deposit mass thereon, and effects thereof may be further monitored.

The operation of the QCM monitor 1 is software-controlled. Operating parameters are first configured and stored in a battery-backed RAM 16 at addresses above the microprocessor 10 recognized top of the memory 16. This ensures that the stored operating parameters are not erased by the microprocessor 10 and that they are retained in the event of a power failure. Once the monitor 1 has been configured and is acquiring data, a configuration variable is set. The variable is checked when power is restored to the monitor 1. If the configuration variable is set, the monitor 1 automatically continues acquiring data using the same operating parameters. This ensures that, in the event of a loss of power, the monitor 1 continues operating when the power is restored. Furthermore, the battery-backed real time clock 24 date/time stamps the data to ensure proper logging of the data. As a result, complete loss of data can be avoided.

The monitor 1 also performs error trapping on two levels in the monitor 1. First, a watch dog timer circuit 26 is used to reset the microprocessor 10 if it gets into an unpredictable state. The watch dog timer circuit 26 is configured to require a reset signal within 1.6 seconds. If the watch dog timer circuit 26 does not see the reset stoke command within 1.6 seconds, the microprocessor 10 is reset. The second level of error trapping is performed using an instruction which transfers programmed execution to a specific location in the event that an arithmetic error occurs. Such an instruction causes the microprocessor 10 to restart. These levels of error trapping ensure that the monitor 1 does not hang when an unpredictable state is encountered.

As previously discussed, communication with the monitor 1 is performed with the local keypad 20 and the LCD 22 or a remote device connected through a communication port of the monitor 1. The communication port can be used for remote communication via a personal computer or other auxiliary device 25. The local keypad 20, in a preferred embodiment, is matrix addressed to re-map the default key values to a more familiar telephone numerical keypad arrangement. The additional six keys available on the keypad 20 are used for a data entry key, a clear entry key, and for special routine and for option verification via a yes/no input. When the monitor 1 is expecting a numerical input, all non-numerical keys are ignored. The sub-routine is the routine which polls the keypad 20 and the auxiliary inputs for data. Data is accumulated until an enter indication is detected. The input number string is then converted to a number, and control is returned to the calling routine. Data may be accepted equally from either the keypad 20 or the auxiliary device 25 connected to the auxiliary input.

Various menu options are available to a user, such as set date/time, set program parameters, display program parameters, start analysis, retrieve data, and the like. When the monitor 1 is first started, only the set date/time and set program parameters are recognized. After the program parameters are configured, all options are recognized. This enables the parameters to be reviewed before analysis is started. After an analysis has been started, displaying of program parameters, starting analysis or retrieving data, may be performed. Retrieving data clears the data buffer without saving the data. A hidden data retrieval option is also available to enable a user to retrieve data after requesting to clear the data buffer within the retrieving data option. This ensures that data can be retrieved after a data buffer is cleared in the retrieve data option. The set date/time option requests a user to input the current time in hours and minutes. Then, the current date by month, day and year is entered. The real time clock 24 of the microprocessor 10 may then be set with these parameters.

In the set program parameters option, several parameters are requested from the operator. First, the number of integration periods to be averaged is requested. In an embodiment, a maximum of twenty integrations can be averaged. Then, the analysis period in minutes can be entered. Although the monitor 1 performs an analysis every sixty seconds, data may only be stored on the analysis period interval. This number can range from one through 255 minutes. Third, the probe constants for the four probes 12 must be input. The probe factors are used to correlate the observed frequency shift of each probe 12 to mass of the deposit. The probe factors are obtained during the probe calibration procedure.

The final program parameter is the output filter factor. The analog output can be filtered using a moving average filter with a period ranging from one to ten. A filter period of one indicates that the output is not filtered. The technique of filtering minimizes spurious output spikes in favor of a smooth curve. After the programmed parameters are entered, the display program parameter option can be used to review the entered parameters.

Next, data acquisition may be initiated by the starting analysis option. The start analysis requires the operator to use a specific key on the keypad 20 to start and/or abort the analysis. When the monitor 1 is running, data must be retrieved before another acquisition can be started. When retrieval of data is completed, the monitor 1 may be stopped.

Data may be retrieved through the auxiliary port to a personal computer or other auxiliary device 25 capable of retrieving data from the QCM monitor 1. Once a communication link between the monitor 1 and the personal computer 25 has been verified, the operator is prompted for a file name to be used for data storage on the personal computer 25 and an identifier string for the data. The QCM monitor then reads the stored data from the buffer and transmits the information to the personal computer 25.

The main data acquisition sub-routine controls data acquisition initiation, termination as well as the timing protocol for data acquisition. Upon entering this sub-routine, the user is prompted to hit the appropriate keys to start or abort data acquisition. Frequency data are collected for the number of iterations requested in the sub-menu. Then, average frequencies for each of the four channels may be calculated. The initial frequencies, $f_{n(t=0)}$ are stored in the RAM 16 and are used to calculate subsequent frequency shifts as follows:

$$-\Delta f_n(t) = f_n(0) - f_n(t)$$

where t is the elapsed time relative to time=0.

Another sub-routine is then called to calculate the mass of deposit adherent on the probe surface. This mass, computed in micrograms, is calculated from the frequency shift and the probe factor as follows:

$$\Delta m_n = PF_n \times -\Delta f_n$$

The mass and time data are then stored in the data buffer and displayed on the LCD 22 and through the port to the remote device 26, if present. Finally, the analog outputs are set through another sub-routine. At this time, the instrument configuration variable is set to indicate that the instrument was running. Should a power failure occur at any time following this point, the instrument would continue operating using the configured parameters.

The sub-routine may then enter a continuous loop which monitors the status of one of the ports and polls the keypad 20 and the auxiliary port for a command. Issuing an "abort" on the local keypad 20 or a "quit" through the auxiliary interface exits the data acquisition routine and requests that data be downloaded to a remote device, as previously discussed.

Frequency data is used to calculate a new mass for each probe 12, and the display and analog outputs are updated. Data is only stored on the intervals requested by the operator. The data acquisition loop continues to acquire data until either a quit is requested by a user or the data buffer is filled. In either instance, in a preferred embodiment, the program requests that the data is downloaded.

A test of the monitor 1 is performed by increasing the interfacial mass on the probe surface through the galvanic electrodeposition of copper onto the gold electrodes. The supply current in the tests is varied to change the deposition rate observed by the QCM monitor 1. Due to the redundancy of the data acquisition program and instrument hardware, copper deposition is performed on a single probe only. The other three probes are left to oscillate in air. No mass change is observed for these three probes within ±0.01 micrograms which is less than the detection limit of 0.5 micrograms.

Figure 4:
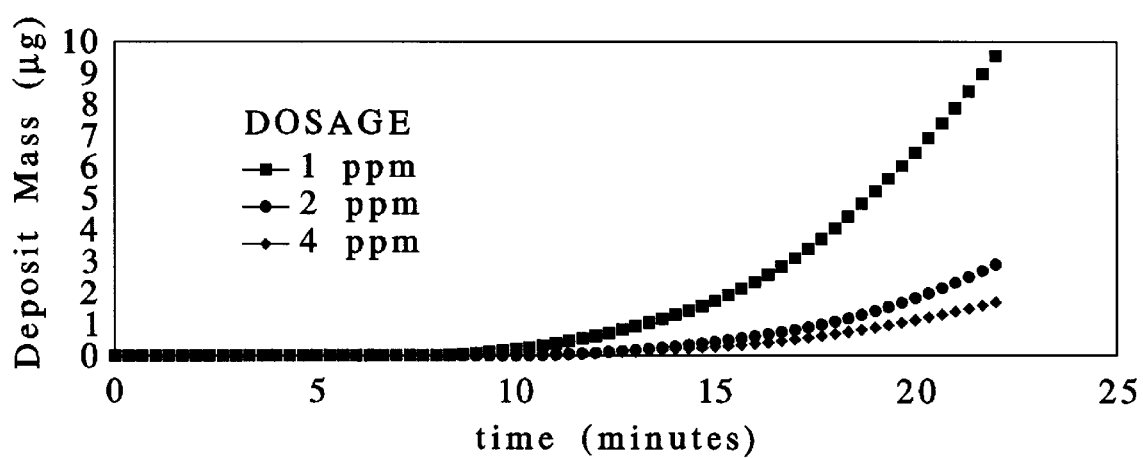
FIG. 4 illustrates a graph illustrating the actual mass plotted over time in process water when anti-scalant treatment dosage is varied.

FIG. 4 shows a graph of deposit mass on the probe 12 in micrograms recorded by the QCM monitor 1 over time in minutes. The mass is recorded by a data logger connected to an analog output of the probe 12. The deposit mass on the probe 12 is calculate using the following equation:

$$\Delta m = PF_N \times -\Delta f_n$$

FIG. 4, therefore, illustrates actual scale deposition data using the actual response of the QCM monitor 1 in process water when anti-scalant treatment dosage is varied.

The QCM monitor 1 may also compensate for temperature based on the temperature dependence of the probe frequency. The temperature dependence of the crystal oscillation frequency is approximately 2 ppm/°C. over the temperature range of 21° C. to 66° C. In systems with wide temperature swings, the temperature dependence of the oscillation frequency required temperature compensation to obtain accurate deposition data. This factor can be incorporated in such systems with wide temperature swings.

As a result of the foregoing, a QCM scale rate monitor 1 is provided capable of measuring the rate of scale deposition in a flowing stream and for the measurement for the effects of crystal modifiers, scale inhibitors, and anti-scale compounds on the rate of scale deposition in a flowing stream. The QCM monitor 1 is, therefore, a highly sensitive instrument for measuring interfacial mass on the surface of a piezoelectric quartz crystal or probe 12. A change in oscillating frequency of the probe 12 is directly proportional to the change in interfacial mass on the surface of the probe 12.

The QCM monitor 1 may also be used to measure the effect of various scale inhibitors and dispersants on the formation and deposition rate of calcium carbonate scale. The QCM monitor 1 can detect both biological and non-biological filing. With adaptations, the QCM monitor 1 can be used to screen several products at the same time. A significant advantage of the present invention is that both toxic biocides and non-toxic dispersants or treatments against the sessile population can be shown in an economical, rapid and easy manner.

In another embodiment of the present invention, the monitor 1 is provided to measure in real time the efficacy of scale control compounds in process water streams and to control chemical feed pump rates as a function of scale control efficacy in particular water process streams. The monitor 1 uses two QCM-based scale rate monitor probes 12 in series to measure scale deposition rates in a water stream before and after chemical treatment. The ratio of the scale deposition rate in the treated water and that in the untreated water is used to determine product efficacy as a percent of scale growth inhibition. The percent scale growth inhibition at a particular anti-scalant dosage level can then be used for either choosing the best product for a particular process stream or for controlling product dosage to inhibit all scale growth in such a water stream.

To this end, in an embodiment, a solution of $Na_2CO_3$ can be injected into the water stream, tested by the monitor 1 to enhance the deposition of $CaCO_3$ and thereby facilitate a quicker measurement. The monitor 1, therefore, can be used to make product comparisons quickly in real process water. For example, measurements needed to compare three products at four dosage levels can be made in one day using this monitor 1. Anti-scalant efficacy can further be continuously monitored in real time in actual process water streams. A chemical feed pump or other feeder 28 can be automatically adjusted in order to attain an acceptable scale growth inhibition level based on the monitored efficacies.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for feeding a product into a process stream, the system comprising:

first sensing means in communication with the process stream capable of detecting a change in frequency in the process stream and producing a first signal indicative of the change;

second sensing means in communication with the process stream capable of detecting a change in frequency in the process stream and producing a second signal indicative of the change;

processing means receiving the first signal from the first sensing means and capable of producing a third signal indicative of a quantity of mass on the first sensing means in the process stream, the processing means also receiving the second signal from the second sensing means and capable of comparing the first signal and the second signal and generating a fourth signal indicative of a difference in mass quantities on the first and second sensing means; and feeding means operatively connected to the processing means and capable of receiving the third and fourth signals from the processing means wherein the feeding means initially feeds the product into the process stream upon receipt of the third signal and controls the feed of the product based on the fourth signal.

2. The system of claim 1 wherein the feeding means feeds the product into the process steam only due to a predetermined magnitude of the signal indicative of a predetermined quantity of mass.

3. The system of claim 1 further comprising:

display means operatively connected to the processing means capable of displaying the change in frequency and/or the quantity of mass.

4. A system for measuring anti-scalant efficacy or biocide or non-toxic dispersant on-line, in a process stream, the system comprising:

a first sensing means detecting frequency change in the process stream and producing a signal indicative thereof;

processing means receiving a signal from the first sensing means and producing a feed signal;

feeding means responsive to the feed signal and capable of feeding a product into the process stream as a result of the feed signal; and a second sensing means capable of detecting frequency change in the process stream after feeding the product into the processing means and producing a signal indicative thereof wherein the processing means is capable of receiving the signal from the second sensing means to compare with the signal from the first sensing means to provide an indication of the efficacy of the product in the process stream.

5. The system of claim 4 further comprising:

output means capable of displaying the frequency changes and the efficacy.

6. A method for controlling product feed into a process stream, the method comprising the steps of:

monitoring scale deposition or biofilm build-up on a first probe placed in the process stream and producing a first signal indicative thereof;

feeding a product into the process stream;

monitoring scale deposition on a second probe placed in the process stream after the product is fed in the process stream and producing a second signal indicative thereof;

determining efficacy of the product in the process stream by comparing the first signal with the second signal; and controlling feed of product based on the determined efficacy.

7. The method of claim 6 wherein the efficacy is determined in real time.

8. The method of claim 6 further comprising the step of:

adjusting the feed to attain an acceptable scale or biofilm growth inhibition.

* * * * *